(12) United States Patent
Brueck et al.

(10) Patent No.: US 9,403,842 B2
(45) Date of Patent: Aug. 2, 2016

(54) PRASUGREL IN NON-CRYSTALLINE FORM AND PHARMACEUTICAL COMPOSITION THEREOF

(75) Inventors: Sandra Brueck, Ottenhofen (DE); Jana Paetz, Bonn (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 13/389,407

(22) PCT Filed: Aug. 4, 2010

(86) PCT No.: PCT/EP2010/061348
§ 371 (c)(1),
(2), (4) Date: Feb. 27, 2012

(87) PCT Pub. No.: WO2011/015599
PCT Pub. Date: Feb. 10, 2011

(65) Prior Publication Data
US 2012/0149727 A1 Jun. 14, 2012

(30) Foreign Application Priority Data
Aug. 7, 2009 (DE) .................. 10 2009 036 646

(51) Int. Cl.
*C07D 495/04* (2006.01)
*A61K 9/14* (2006.01)
*A61K 9/16* (2006.01)
(Continued)

(52) U.S. Cl.
CPC .............. *C07D 495/04* (2013.01); *A61K 9/145* (2013.01); *A61K 9/146* (2013.01); *A61K 9/1617* (2013.01); *A61K 9/1641* (2013.01); *A61K 9/1652* (2013.01); *A61K 9/2027* (2013.01); *A61K 9/2054* (2013.01); *A61K 9/2077* (2013.01); *A61K 31/4365* (2013.01)

(58) Field of Classification Search
CPC . A61K 9/1641; A61K 9/2031; A61K 9/2077; A61K 9/2013; A61K 9/1617; A61K 9/1652; A61K 9/145; A61K 9/2054; A61K 31/4365; C07D 495/04
See application file for complete search history.

(56) References Cited

U.S. PATENT DOCUMENTS

| 6,693,115 | B2 | 2/2004 | Asai et al. | |
|---|---|---|---|---|
| 2009/0281136 | A1* | 11/2009 | Mhetre et al. | ................. 514/301 |
| 2011/0003847 | A1* | 1/2011 | Doser | ........................... 514/301 |

FOREIGN PATENT DOCUMENTS

| CA | 2671975 | 6/2008 |
|---|---|---|
| CA | 2672134 | 6/2008 |
| CA | 2672154 | 6/2008 |

(Continued)

OTHER PUBLICATIONS

Troy et al. "Remington: The Science and Practice of Pharmacy", pp. 2393 (2006).*

(Continued)

*Primary Examiner* — Ernst V Arnold
*Assistant Examiner* — Kyung Sook Chang
(74) *Attorney, Agent, or Firm* — Chalin A. Smith; Smith Patent

(57) ABSTRACT

The present invention relates to prasugrel or a pharmaceutically compatible salt thereof, compositions that contain this active substance and pharmaceutical compositions that contain this active substance or a composition containing this active substance. The present invention further relates to methods for producing the novel compositions.

19 Claims, 7 Drawing Sheets

(51) Int. Cl.
*A61K 9/20* (2006.01)
*A61K 31/4365* (2006.01)

(56) References Cited

FOREIGN PATENT DOCUMENTS

| CA | 2672157 | 6/2008 | | |
|---|---|---|---|---|
| EP | 2100609 A1 | * | 9/2009 | |
| JP | WO 2008072535 A1 | * | 6/2008 | ........... A61K 9/2054 |
| JP | EP 2100610 A1 | * | 9/2009 | ........... A61K 9/2054 |
| SI | P-200900040 | | 2/2009 | |
| SI | P-200900155 | | 6/2009 | |
| SI | P-200900194 | | 7/2009 | |
| WO | WO 2006/135605 | | 12/2006 | |
| WO | WO 2009/062044 | | 5/2009 | |
| WO | WO 2009/098142 | | 8/2009 | |
| WO | WO 2010/094471 | | 2/2010 | |
| WO | WO 2010/070677 | | 6/2010 | |

OTHER PUBLICATIONS

Hiller, "Polyvinylpyrrolidone Excipients for Pharmaceuticals", pp. 84-85 (2005).*

Khadka et al. "Pharmaceutical particle technologies: An approach to improve drug solubility, dissolution and bioavailability", Asian Journal of Pharmaceutical Sciences, vol. 9, pp. 304-316 (2014).*

Liu, "Water-Insoluble Drug Formulation", second edition (google ebook), CRC Press, Jan. 18, 2008, pp. 501-504.*

Leuner, C. et al., *European Journal of Pharmaceutics and Biopharmaceutics*, Elsevier Science Publishers, Amsterdam, NL, vol. 50, No. 1, pp. 47-60 (Jul. 3, 2000).

P. Heinrich Stahl, et al. (ed), *Handbook of Pharmaceutical Salts: Properties, Selection and Use*, VHCA, Zurich, Switzerland (2002), pp. 1-7.

Aateka Patel et al, "Pharmaceutical Salts: A Formulation Trick or a Clinical Conundrum?", British Journal Cardiology (2009), vol. 16, pp. 281-286.

"Amorphous Solids: Implications for Solubility and Stability", SSCI Inc. (2003) http://www.ssci-inc.com/Information/RecentPublications/ApplicationNotes/AmorphousSolidsImplications/tabid/142/Default.aspx.

Sameer Singh et al., "A Review on Solid Dispersion", International Journal of Pharmacy and Life Sciences, Sep. 2011, vol. 2, Issue No. 9, pp. 1078-1095.

"Solid Solution": en.wikipedia.org/wiki/Solid_solution.

* cited by examiner

Fig. 1a

| Wavenumber [cm⁻¹] | Transmission [%] | Wavenumber [cm⁻¹] | Transmission [%] | Wavenumber [cm⁻¹] | Transmission [%] | Wavenumber [cm⁻¹] | Transmission [%] | Wavenumber [cm⁻¹] | Transmission [%] |
|---|---|---|---|---|---|---|---|---|---|
| 2922.8 | 92.9 | 2817.9 | 93.0 | 2768.0 | 90.9 | 1756.3 | 58.3 | 1702.5 | 49.2 |
| 1612.8 | 92.8 | 1586.1 | 81.7 | 1487.3 | 64.1 | 1459.0 | 76.9 | 1444.4 | 79.3 |
| 1419.0 | 83.9 | 1388.6 | 78.7 | 1367.5 | 71.7 | 1353.2 | 82.9 | 1318.8 | 90.4 |
| 1279.2 | 88.6 | 1253.6 | 73.4 | 1233.4 | 69.3 | 1216.3 | 52.9 | 1191.5 | 30.9 |
| 1127.1 | 57.0 | 1090.0 | 69.5 | 1066.6 | 58.3 | 1049.0 | 62.6 | 1030.2 | 66.1 |
| 1008.7 | 46.1 | 978.1 | 71.2 | 952.7 | 86.9 | 925.8 | 74.2 | 887.7 | 59.3 |
| 829.5 | 59.3 | 801.6 | 59.9 | 757.4 | 42.2 | 733.1 | 69.8 | 694.9 | 76.9 |
| 662.5 | 65.0 | | | | | | | | |

Fig. 2a

| Wavenumber [cm⁻¹] | Transmission [%] | Wavenumber [cm⁻¹] | Transmission [%] | Wavenumber [cm⁻¹] | Transmission [%] | Wavenumber [cm⁻¹] | Transmission [%] | Wavenumber [cm⁻¹] | Transmission [%] |
|---|---|---|---|---|---|---|---|---|---|
| 2917.1 | 94.4 | 2841.6 | 93.8 | 1777.9 | 74.7 | 1758.6 | 70.0 | 1698.3 | 64.2 |
| 1612.7 | 92.2 | 1584.8 | 84.2 | 1487.3 | 65.6 | 1455.6 | 79.1 | 1418.4 | 84.1 |
| 1370.2 | 60.6 | 1176.8 | 36.7 | 1122.0 | 50.9 | 1085.3 | 66.2 | 1046.0 | 72.0 |
| 1012.9 | 52.5 | 895.4 | 69.1 | 838.1 | 79.1 | 805.2 | 66.2 | 758.0 | 39.8 |
| 693.7 | 85.8 | 671.0 | 78.2 | | | | | | |

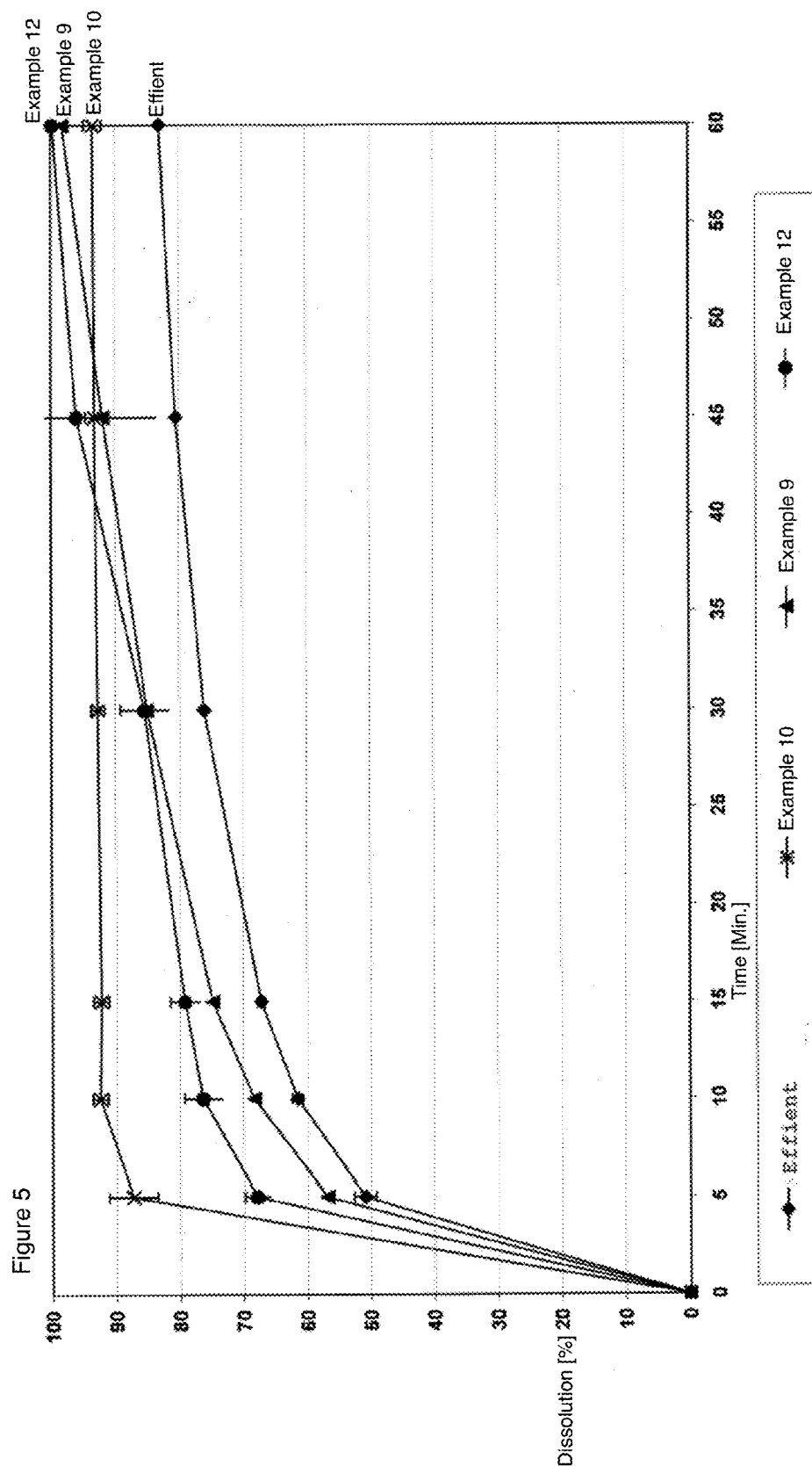

PRASUGREL IN NON-CRYSTALLINE FORM AND PHARMACEUTICAL COMPOSITION THEREOF

This application corresponds to the national phase of International Application No. PCT/EP2010/061348 filed Aug. 4, 2010, which, in turn, claims priority to German Patent Application No. 10 2009 036 646.6 filed Aug. 7, 2009, the contents of which are incorporated by reference herein in their entirety.

The present invention relates to prasugrel or a pharmaceutically compatible salt thereof, compositions that contain this active substance and pharmaceutical compositions that contain this active substance or a composition containing this active substance. The present invention further relates to methods for producing the new compositions.

Prasugrel has the chemical name 2-acetoxy-5-(α-cyclopropylcarbonyl-2-fluorobenzyl)-4,5,6,7-tetrahydrothieno[3,2-c]pyridine. Prasugrel has the following structural formula:

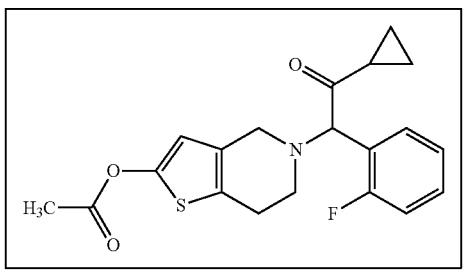 [SMILES: CC(=O)Oc1cc2c(s1)CCN(C(C(=O)C1CC1)c1ccccc1F)C2]

A method for producing crystalline prasugrel is disclosed in EP-A-0 542 411.

Various salts of acid addition of prasugrel are disclosed in EP-A-1 298 132. These are also crystalline salts.

Prasugrel is an orally administered platelet aggregation inhibitor. A problem with this is that prasugrel is a sparingly soluble active substance. The free base of the active substance has a solubility of 57 μg/ml in water, but even the salts display only limited solubility.

The solubility of an active substance can often be increased by micronisation of the particles of active substance. However, because of the pronounced oxidation sensitivity of prasugrel, dry grinding in the μm range is not possible, as there is excessive chemical degradation, caused both by the mechanical and thermal effects, combined with the increase in surface area.

Furthermore, prasugrel also displays degradation that is strongly pH-dependent. At pH values of <3, degradation of more than 1% is observed after just 2 hours. This restricts the possible excipients used in the production of pharmaceutical formulations.

Various proposals have been made in the prior art for improving the solubility of prasugrel from pharmaceutical compositions and for increasing the shelf life of corresponding pharmaceutical compositions. Thus, WO 2008/072535 proposes processing prasugrel together with a low-substituted hydroxypropylcellulose into pharmaceutical compositions. For this, the active substance is mixed intensively with low-substituted hydroxypropylcellulose, hydroxypropylcellulose and lactose for 3 minutes. Magnesium stearate is added to the resultant mixture, and the mixture is mixed again. The powder obtained is compacted to tablets. The prasugrel and hydroxypropylcellulose are mixed in the ratio of about 1:1. Investigations have shown that owing to the mixture ratio of prasugrel to hydroxypropylcellulose and owing to the short mixing time, the polymorphic form of the active substance is not altered in the method disclosed.

Similar pharmaceutical compositions, which in addition to prasugrel contain water-soluble polymers such as hydroxypropylcellulose, hydroxypropylmethylcellulose and carboxymethylcellulose sodium, are disclosed in WO 2008/069262, WO 2008/072532 and WO 2008/072534.

WO 2008/072533 discloses prasugrel-containing pharmaceutical compositions which, in addition to the active substance, contain hydroxypropylcellulose in a weight ratio of about 1:1.5. In this case the mixtures are mixed for 3 minutes with high energy input in a Henschel mixer. In the comparative example presented, a corresponding mixture is mixed for 30 minutes in a diffusion mixer. Once again, it was found that with this mixture ratio of prasugrel to hydroxypropylcellulose and the stated mixing time, no change takes place in the polymorphic form of the active substance.

To increase the shelf life of prasugrel-containing tablets, WO 2008/073759 proposes packaging them in an air-tight, moisture-proof container under a positive liquefied-gas pressure.

Therefore there is still a need for prasugrel-containing formulations that make the active substance available in a form that is as soluble as possible. There is also a need for improvement of the dissolution rate and of the bioavailability of the active substance. Moreover, it is desirable to improve the chemical stability of the active substance, in particular against oxidative degradation and under thermal load. Another problem is improvement of the processability of prasugrel to pharmaceutical compositions and improvement of the shelf life of corresponding compositions.

Now, it was found, surprisingly, that under certain processing conditions prasugrel can be transformed into a non-crystalline form, and this non-crystalline form or compositions that contain this form solve one or a plurality of the aforementioned problems.

The present invention therefore relates to prasugrel or a pharmaceutically compatible salt thereof in non-crystalline form.

In the present text, non-crystalline form means any form of the active substance or a pharmaceutically compatible salt thereof that is substantially free and preferably completely free from crystalline fractions of the active substance or a pharmaceutically compatible salt thereof. Substantially free from crystalline fractions means that the form contains less than 10 wt. %, preferably less than 5 wt. % and most preferably less than 1 wt. % of active substance in crystalline form, wherein the percentages by weight refer to the total amount of prasugrel or of a pharmaceutically compatible salt thereof.

Crystalline fractions of a particular active substance can for example be characterised by DSC measurement or XRPD (X-ray powder diffractometry). Thus, crystalline solids show characteristic peaks in the X-ray powder diffraction pattern, whereas non-crystalline forms do not show corresponding peaks.

Furthermore, the crystalline form can also be distinguished from the non-crystalline form of the active substance for example by IR spectroscopy. FIG. 1 shows the IR spectrum of crystalline prasugrel. FIG. 2 shows the IR spectrum of amorphous prasugrel. Apart from a shift of the peaks, for the amorphous active substance an additional peak is seen at about 1778 cm$^{-1}$, and for the crystalline prasugrel, additionally peaks at about 1254 cm$^{-1}$ and about 830 cm$^{-1}$.

The prasugrel according to the invention or a pharmaceutically compatible salt thereof in non-crystalline form can either be in the form of an amorphous solid or can be in a composition as solid solution or solid dispersion. If the active substance is incorporated in a solid dispersion, after incorporation it is in amorphous form in an excipient, in particular a polymer. "Solid dispersion" therefore means a dispersion of the amorphous active substance in an excipient matrix. Alternatively the amorphous active substance is distributed as a molecular dispersion in the excipient matrix. In this case it is a solid solution of the active substance in the excipient matrix.

In the present text, "active substance" means prasugrel or a pharmaceutically compatible salt thereof. Suitable pharmaceutically compatible salts are for example the hydrochloride, the hydrobromide, the sulphate, the phosphate, alkylsulphonic acid salts, such as methanesulphonate, trifluoromethanesulphonate and ethanesulphonate, arylsulphonic acid salts, such as benzenesulphonate, p-toluenesulphonate, 1-naphthalenesulphonic acid, 2-naphthalenesulphonic acid and 1,5-naphthalenedisulphonic acid, and salts of organic acids, such as acetate, malate, fumarate, succinate, citrate, ascorbate, tartrate, oxalate and maleate. Preferably the active substance according to the present invention is prasugrel base.

According to the invention, it was found, surprisingly, that prasugrel or a pharmaceutically compatible salt thereof can be obtained in non-crystalline form by various methods of production. For example, the active substance can be processed together with a hydrophilic polymer and in this way be amorphised. It is presumed that the presence of the hydrophilic polymer stabilises the metastable state of the active substance. The active substance can be amorphised together with the hydrophilic polymer for example by a melting process or by grinding. In both methods, it was found to be important for sufficient polymer to be present, in order to stabilise the metastable state of the active substance. Moreover, the active substance and the polymer must be mixed together intimately, so that the active substance is transformed into its non-crystalline form. Suitable methods of production are described in more detail below.

In order to make an amount of polymer available that is sufficient to stabilise the metastable, non-crystalline state of the active substance, the weight ratio of prasugrel, based on the free base, to hydrophilic polymer should be <1:4, preferably ≤1:4.5, more preferably ≤1:7.5. Preferred weight ratios are for example about 1:5 or about 1:10. In contrast, grinding with a weight ratio of about 1:1 still does not lead to the desired amorphisation of the active substance.

Suitable hydrophilic polymers are water-soluble polymers, for example polymers that have a water solubility of >0.01 mg/ml at room temperature. One or a plurality of hydrophilic polymers can be processed together with the active substance, into the compositions according to the invention. Moreover, the compositions can contain further pharmaceutically compatible excipients if desired.

Generally the designation "hydrophilic polymer" comprises polymers with polar groups. Examples of polar groups are hydroxyl, amino, carboxyl, carbonyl, ethers, esters, sulphonates. Hydroxyl groups are particularly preferred.

The hydrophilic polymer usually has a molecular weight in the range between 1000 and 250 000 g/mol, preferably 2000 to 100 000 g/mol, and particularly between 4000 and 50 000 g/mol. Moreover, a 2 wt. % solution of the hydrophilic polymer in pure water preferably has a viscosity between 2 and 8 mPas at 25° C. The viscosity is determined according to the European Pharmacopoeia (Ph. Eur.), 6th edition, section 2.2.10.

Moreover, the hydrophilic polymer preferably has a glass transition temperature (Tg) between 20° C. and 150° C., preferably 25° C. to 100° C. The glass transition temperature (Tg) is the temperature at which the hydrophilic polymer becomes brittle on cooling and soft on being heated. This means that above the glass transition temperature the hydrophilic polymer becomes soft and can be deformed plastically without breaking. The glass transition temperature is determined by means of a Mettler-Toledo® DSC 1, using a heating rate of 10° C./min and a cooling rate of 15° C./min.

For example, the hydrophilic polymer can be selected from the group consisting of cellulose derivatives, such as hydroxypropylmethylcellulose, hydroxypropylcellulose, carboxymethylcellulose, preferably as sodium or calcium salt, hydroxyethylcellulose, polyvinylpyrrolidone, preferably with a molecular weight from 10 000 to 60 000 g/ml, copolymers of polyvinylpyrrolidone, preferably copolymers comprising vinylpyrrolidone and vinyl acetate units (e.g. povidone, VA64, BASF), preferably with a molecular weight between 40 000 and 70 000 g/ml, polyoxyethylene-alkyl ethers, polyethylene glycol, block copolymers of ethylene oxide and propylene oxide (poloxamers, Pluronic), polyoxyglycerides, e.g. PEG-glyceryl stearate (Gelucire), polymethacrylate derivatives, polyvinyl alcohol, polyvinyl alcohol derivatives and polyethylene glycol derivatives, such as PEG-glyceryl stearate. Preferred hydrophilic polymers are PEG-glyceryl stearate, block copolymers of ethylene oxide and propylene oxide, polyethylene glycol and hydroxypropylmethylcellulose.

In one embodiment, the composition according to the invention can be produced by a melting process. In this, a solid solution or solid dispersion of the active substance is obtained in a matrix of the hydrophilic polymer. The solid solution or solid dispersion is preferably in the form of fusion granules.

For production of the compositions according to the invention by melting processes, hydrophilic polymers with a melting point of <120° C. are particularly suitable. The melt of hydrophilic polymer and active substance may have a eutectic melting point. This effect can be counteracted by adding higher-melting excipients, in particular with a specific surface of >1.5 m$^2$/g (measured according to European Pharmacopoeia 6.0, 2.9.26). Suitable corresponding excipients are for example microcrystalline cellulose, colloidal silica (Aerosil) and calcium phosphate. Lower and higher melting polymers can also be combined for preparing the polymer melt. There is also the possibility of preparing pre-emulsions or pre-suspensions using higher melting polymers, with subsequent lyophilisation.

Moreover, it may be advantageous to mix a sugar alcohol and/or a cellulose into the polymer melt, for example Isomalt, mannitol, sorbitol or xylitol or microcrystalline cellulose. These excipients act as structure-forming agents and/or binders and are used for improving the processability of the composition both during lyophilisation and subsequent compression.

The present invention therefore also relates to a method of production of a composition described above, wherein the method comprises dissolving or dispersing prasugrel or a pharmaceutically compatible salt thereof in a melt of the hydrophilic polymer and cooling the solution or dispersion to obtain a solid. The solution or dispersion can, optionally after being suspended in a liquid, such as ethanol, be dispersed in another liquid, preferably water, and then lyophilised.

The present invention also relates to compositions such as are obtainable by the method described above.

In an alternative embodiment the non-crystalline form of the active substance can be obtained by a grinding process in the presence of the hydrophilic polymer. The grinding can be dry grinding or wet grinding. The grinding step can be followed by further processing steps, for example lyophilisation, spray drying or granulation on a carrier.

In addition to the weight ratio of active substance to hydrophilic polymer described above, sufficiently long grinding of the active substance-polymer mixture is necessary, in order to transform the active substance to its non-crystalline, in particular amorphous form. A suitable duration can be determined, by a person skilled in the art, from whether the crystalline active substance used is in the amorphous form after the grinding step. The duration of the grinding step must be increased if necessary. Grinding for at least 1 h, preferably at least 2 h leads as a rule to the desired amorphisation of the active substance.

As well as the one or a plurality of hydrophilic polymers, when it is produced by grinding, the composition according to the invention can contain further, pharmaceutically compatible excipients. Emulsifiers, for example, in particular with HLB value >12, are particularly suitable. The amount and nature of the hydrophilic polymers and other excipients used have an influence on the release and stabilisation of the amorphous form of the active substance.

The present invention therefore also relates to a method of production of a composition described above, comprising dry or wet grinding of prasugrel or of a pharmaceutically compatible salt thereof in the presence of the hydrophilic polymer. If the grinding step is dry grinding, this is preferably carried out with cooling, for example by means of liquid nitrogen. In a preferred embodiment, grinding takes place by dry grinding in a ball mill with cooling with liquid nitrogen for a period of at least 1 h, preferably at least 2 h.

The present invention further relates to a composition obtainable by the method described above.

The active substance in non-crystalline form described above or the compositions described above can then be further processed using further pharmaceutically compatible excipients into pharmaceutical compositions, in particular for inhibition of platelet aggregation. The finished dosage forms can be e.g. tablets, capsules, sachets or powders.

The pharmaceutical composition can, in addition to the hydrophilic polymer, contain one or a plurality of further pharmaceutically acceptable excipients, e.g. fillers, lubricants, flow regulators, separating agents, disintegrants (Lexikon der Hilfsstoffe für Pharmazie, Kosmetik and angrenzende Gebiete [*Dictionary of excipients for pharmacy, cosmetics and related areas*], published by H. P. Fiedler, 4th edition, and "Handbook of Pharmaceutical Excipients", 3rd edition, by Arthur H. Kibbe, American Pharmaceutical Association, Washington, USA and Pharmaceutical Press, London).

Fillers: the pharmaceutical composition can contain one or a plurality of fillers. Generally a filler is a substance that increases the bulk volume of the mixture and therefore the size of the resultant pharmaceutical form. Preferred examples of fillers are lactose and calcium hydrogen phosphate. The filler can have a proportion from 0 to 80 wt. %, preferably between 10 and 60 wt. % of the total weight of the composition.

Lubricants: the function of the lubricant is to ensure that tablet compression and ejection take place with low friction between the solid substances and the walls. The lubricant is preferably an alkaline-earth metal stearate, such as magnesium stearate or a fatty acid, such as stearic acid. The lubricant is usually present in an amount from 0 to 2 wt. %, preferably between 0.5 and 1.5 wt. % of the total weight of the pharmaceutical composition.

Disintegrant: disintegrant usually means a substance that is able to break the tablet up into smaller parts, as soon as it is in contact with a liquid. Preferred disintegrants are croscarmellose sodium, sodium carboxymethyl starch, crosslinked polyvinylpyrrolidone (crospovidone) or sodium carboxymethyl glycolate (e.g. Explotab) and sodium bicarbonate. The disintegrant is normally present in a proportion from 0 to 20 wt. %, preferably between 1 and 15 wt. % of the total weight of the composition.

Flow regulators: colloidal silica, for example, can be used as flow regulator. Preferably the flow regulator is present in an amount from 0 to 8 wt. %, more preferably in an amount between 0.1 and 3 wt. % of the total weight of the composition.

Moreover, in addition to prasugrel in non-crystalline form, the pharmaceutical composition can also contain one or a plurality of further active substances in free form or in the form of their pharmaceutically acceptable salts. This can be in particular a coagulation inhibitor, e.g. rivaroxaban, apixaban, dabigatran, edoxaban, betrixaban, eribaxaban or YM-150, or a platelet aggregation inhibitor, e.g. ticlopidine, clopidogrel, dipyridamole or acetylsalicylic acid. Particularly preferably the pharmaceutical composition contains acetylsalicylic acid as further active substance.

Figure 4:
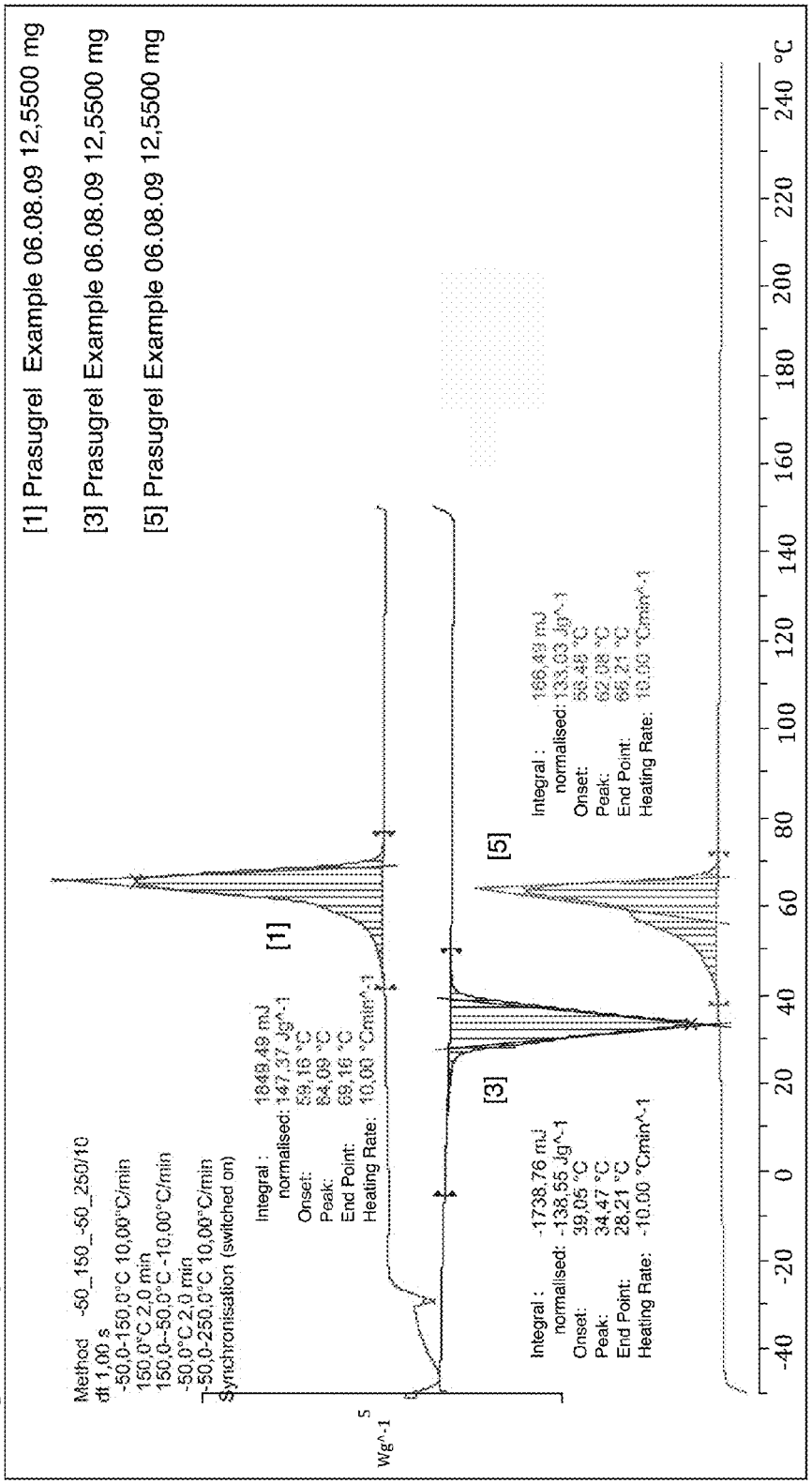

FIG. 4 shows the DSC curve of prasugrel-containing fusion granules according to example 10, and FIG. 5 shows the dissolution profiles of the compositions of examples 9, 10 and 12 compared with the commercial product Effient®.

The present invention will be explained in more detail with the following examples, which are not to be interpreted as limiting.

In addition to the active substance, the following compounds are used in the examples:

Gelucire: PEG-glyceryl stearate

Pluronic: block copolymers of ethylene oxide and propylene oxide

Avicel: microcrystalline cellulose

PEG: polyethylene glycol

Solutol: PEG-hydroxystearate

HPMC: hydroxypropylmethylcellulose

Kollidon: polyvinylpyrrolidone

SDS: sodium lauryl sulphate

In examples 1-10, the active substance is dispersed or dissolved in a melt of the polymer. For further processing the melt is comminuted and compressed with suitable excipients.

EXAMPLE 1

| | |
|---|---|
| Prasugrel base | 5 mg |
| PEG 6000 | 25 mg |

EXAMPLE 2

| | |
|---|---|
| Prasugrel base | 5 mg |
| Gelucire 50/13 | 25 mg |

EXAMPLE 3

| Prasugrel base | 5 mg |
|---|---|
| Gelucire 50/13 | 12.5 mg |
| Pluronic F68 | 25 mg |

EXAMPLE 4

| Prasugrel base | 5 mg |
|---|---|
| Pluronic F68 | 25 mg |

EXAMPLE 5

| Prasugrel base | 5 mg |
|---|---|
| Gelucire 50/13 | 50 mg |

EXAMPLE 6

| Prasugrel base | 5 mg |
|---|---|
| PEG 6000 | 50 mg |
| PEG 400 | 5 mg |

EXAMPLE 7

| Prasugrel base | 5 mg |
|---|---|
| Gelucire 50/13 | 25 mg |
| Pluronic F68 | 25 mg |

EXAMPLE 8

| Prasugrel base | 5 mg |
|---|---|
| Pluronic F68 | 50 mg |

EXAMPLE 9

| Prasugrel base | 5 mg |
|---|---|
| Gelucire 50/13 | 50 mg |
| Avicel 101 | 35.8 mg |

EXAMPLE 10

| Prasugrel base | 5 mg |
|---|---|
| PEG 6000 | 50 mg |
| Solutol HS | 1.5 mg |

Further processing to tablets with the following excipients:

| Kollidon CL | 50.7 mg |
|---|---|
| Avicel PH 101 | 15.5 mg |
| Magnesium stearate | 1.45 mg |

The melt of active substance, PEG 6000 and Solutol HS is comminuted, passed through a 630 μm sieve, mixed with the remaining excipients and compressed to 7 mm tablets.

Figure 1:
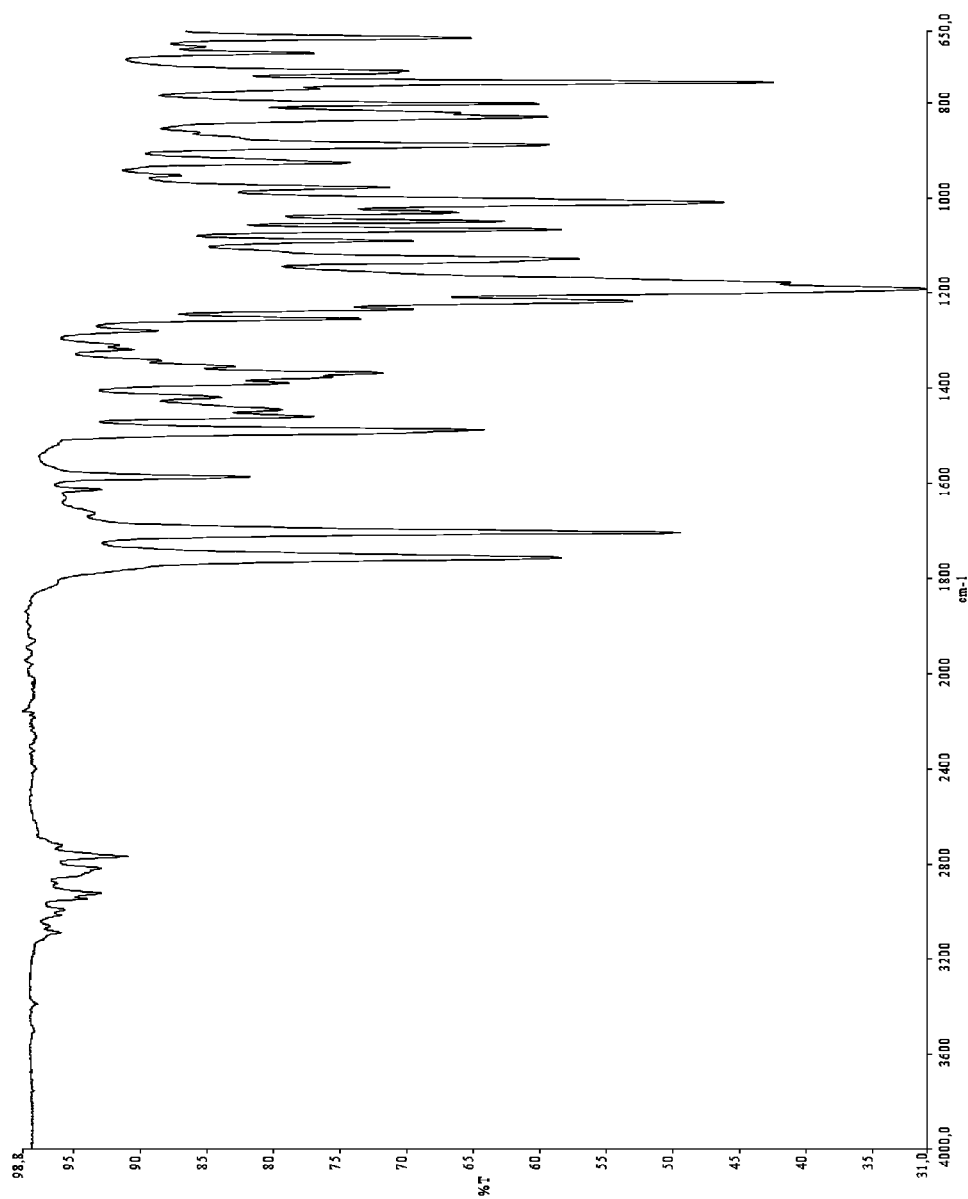
FIG. 1 shows the IR spectrum of crystalline prasugrel.
Figure 2:
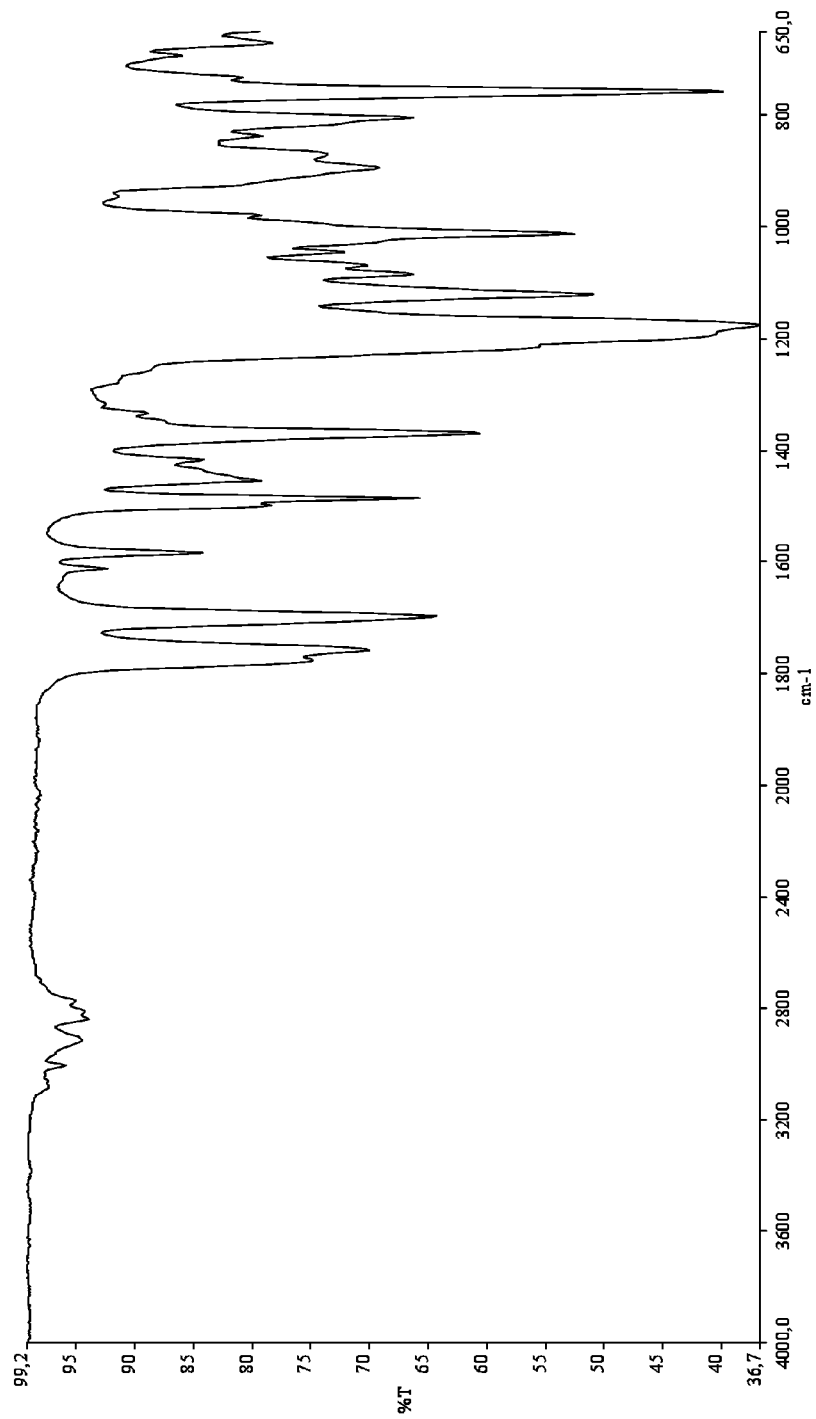
FIG. 2 shows the IR spectrum of amorphous prasugrel.
Figure 3:
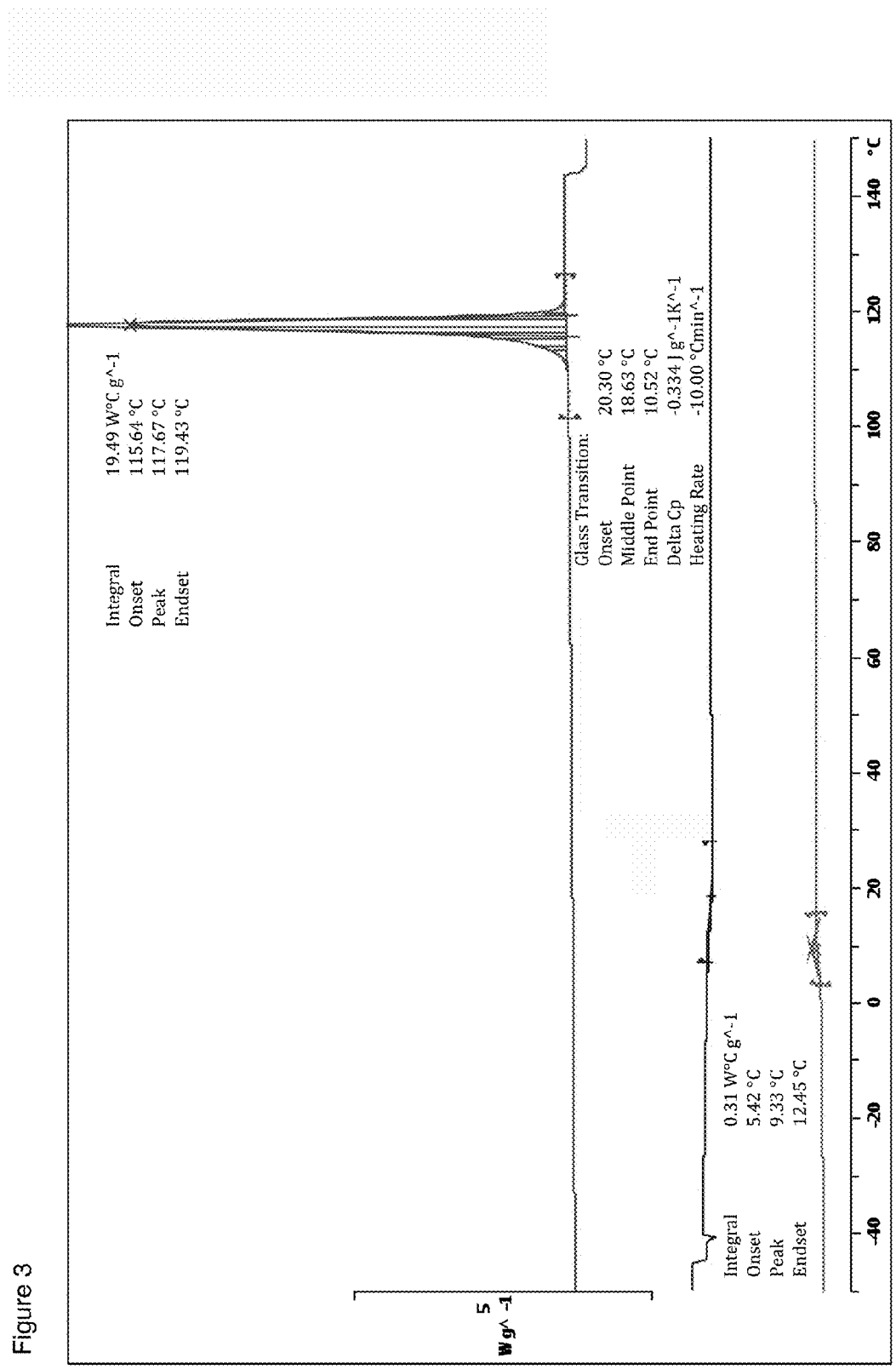
FIG. 3 shows the DSC curve of crystalline prasugrel.

Amorphisation of the active substance by incorporation in the PEG melt is confirmed by DSC measurements. FIG. 3 shows the DSC curve for the active substance used (heating, cooling and heating again). The curve proves that the active substance used is in crystalline form. FIG. 4 shows the DSC curve of the fusion granules obtained (heating, cooling and heating again). The curve proves that the crystalline active substance used is present in the fusion granules in non-crystalline form.

EXAMPLE 11

| Prasugrel base | 5 mg |
|---|---|
| Gelucire 55 | 50 mg |
| Isomalt PF | 50 mg |
| Ethanol 96% | 10 mg |
| Water | 250 mg |

Gelucire is melted at 80° C. Isomalt and prasugrel base are suspended in the melt. 96% ethanol is added. The suspension is dispersed in water using the Ultraturrax. Then it is lyophilised.

EXAMPLE 12

| Prasugrel base | 5 mg |
|---|---|
| Gelucire 55 | 50 mg |
| Avicel PH 101 | 35.80 mg |
| Ethanol 96% | 10 mg |
| Water | 250 mg |

Gelucire is melted at 80° C. Avicel and prasugrel base are suspended in the melt. After adding 96% ethanol, the suspension is dispersed in water and then lyophilised.

In examples 13 and 14 the mixture of the constituents is ground in a ball mill, while cooling with liquid nitrogen.

EXAMPLE 13

| Prasugrel base | 5 mg |
|---|---|
| HPMC 603 | 50 mg |

EXAMPLE 14

| Prasugrel base | 5 mg |
|---|---|
| Pluronic | 50 mg |

EXAMPLE 15

| Prasugrel base | 10 mg |
|---|---|
| Pharmacoat 603 (HPMC) | 50 mg |
| SDS | 2.5 mg |

The active substance is ground with HPMC and SDS in a Netzsch MicroCer at a rotary speed of 3000/min in water.

The resultant suspension is either lyophilised, spray-dried or granulated on a mixture of Avicel and HPMC.

The spray-dried material is mixed with 12 mg croscarmellose, 100 mg Avicel PH 101 and 1.2 mg magnesium stearate and compressed to 7 mm tablets.

EXAMPLE 16

The dissolution rate of the compositions obtained in examples 9, 10 and 12 was determined and compared with the dissolution rate of commercial 5 mg prasugrel tablets (Effient®). The dissolution rate was determined in 900 ml buffer solution (pH value 4.5) at 37° C. by the US Paddle Method (75 rpm; App. II). The results are presented in the following table, which gives the dissolution as percentage of the total amount of active substance.

The dissolution profiles obtained from the measurements are presented in FIG. 5.

| Time [min] | Example 9 | Example 10 | Example 12 | Effient ® |
|---|---|---|---|---|
| 0 | 0 | 0 | 0 | 0 |
| 5 | 57 | 87 | 68 | 51 |
| 10 | 68 | 93 | 76 | 62 |
| 15 | 75 | 92 | 79 | 67 |
| 30 | 85 | 93 | 86 | 76 |
| 45 | 92 | 93 | 96 | 81 |
| 60 | 98 | 93 | 100 | 83 |

It can be seen that, compared with the commercial prasugrel product, the compositions according to the invention provide faster release of the active substance.

The invention claimed is:

1. A composition containing an amorphous form of prasugrel base in combination with a hydrophilic polymer, wherein:
   said prasugrel base is mixed with said hydrophilic polymer to yield a solid solution or solid dispersion;
   the weight ratio of prasugrel base to hydrophilic polymer is less than 1:4; and
   the hydrophilic polymer is selected from the group consisting of cellulose derivatives, polyvinylpyrrolidone, copolymers of polyvinylpyrrolidone, polyoxyethylene-alkyl ether, polyethylene glycol, block copolymer of ethylene oxide and propylene oxide, polyoxyglycerides, polymethacrylate derivatives, polyvinyl alcohol, polyvinyl alcohol derivatives and polyethylene glycol derivatives.

2. The composition according to claim 1, in which the hydrophilic polymer has a glass transition temperature (Tg) between 20° C. and 150° C.

3. The composition according to claim 1, in the form of fusion granules.

4. The composition according to claim 1, wherein said composition further comprises a sugar alcohol and/or a cellulose.

5. A method of producing the composition according to claim 1, said method comprising the steps of dissolving or dispersing an amorphous form of prasugrel base in a melt of the hydrophilic polymer and cooling the solution or dispersion to a solid.

6. The method according to claim 5, in which the solution or dispersion is dispersed in a liquid and is then lyophilised.

7. A composition comprising an amorphous form of prasugrel base in combination with a hydrophilic polymer in the form of a solid solution or solid dispersion, wherein said composition is obtained according to the method of claim 5.

8. A method of producing the composition according to claim 1, said method comprising the step of dry or wet grinding said amorphous form of prasugrel base in the presence of said hydrophilic polymer.

9. The method according to claim 8, wherein the step of dry grinding takes place with a cooling step.

10. The method according to claim 9, wherein the step of dry grinding takes place in a ball mill with liquid nitrogen for a period of at least 1 h.

11. A composition comprising an amorphous form of prasugrel base in combination with a hydrophilic polymer in the form of a solid solution or solid dispersion, wherein said composition is obtained by the method according to claim 8.

12. A pharmaceutical composition comprising the composition according to claim 1 in combination with one or a plurality of pharmaceutically compatible excipients.

13. A method of inhibiting platelet aggregation comprising the step of administering a therapeutically effective amount of the pharmaceutical composition of claim 12 to a subject in need thereof.

14. The composition according to claim 1, wherein said hydrophilic polymer is a cellulose derivative selected from the group consisting of hydroxypropylmethylcellulose, hydroxypropylcellulose, carboxymethylcellulose, and hydroxyethylcellulose.

15. The composition of claim 14, wherein said carboxymethylcellulose is the sodium or calcium salt of carboxymethylcellulose.

16. The composition according to claim 1, wherein said hydrophilic polymer is a copolymer of polyvinylpyrrolidone comprising vinylpyrrolidone and vinylacetate units.

17. The composition according to claim 2, wherein the hydrophilic polymer has a glass transition temperature (Tg) between 25° C. and 100° C.

18. The method according to claim 10, wherein the liquid in which said solid solution or dispersion is dispersed is water.

19. The method according to claim 10, wherein the dry grinding takes place in a ball mill with cooling with liquid nitrogen for a period of at least 2 h.

* * * * *